US009759649B2

(12) United States Patent
Haghgooie et al.

(10) Patent No.: US 9,759,649 B2
(45) Date of Patent: Sep. 12, 2017

(54) SYSTEM AND METHOD FOR INTEGRATED MULTIPLEXED PHOTOMETRY MODULE (71) Applicant: THE GENERAL HOSPITAL CORPORATION, Boston, MA (US)

(72) Inventors: Ramin Haghgooie, Arlington, MA (US); Kenneth T. Kotz, Auburndale, MA (US); Robert Granier, Boston, MA (US); Anne Celia Petrofsky, Sudbury, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 14/443,915

(22) PCT Filed: Nov. 18, 2013

(86) PCT No.: PCT/US2013/070555
§ 371 (c)(1),
(2) Date: May 19, 2015

(87) PCT Pub. No.: WO2014/078785
PCT Pub. Date: May 22, 2014

(65) Prior Publication Data
US 2015/0285731 A1 Oct. 8, 2015

Related U.S. Application Data (60) Provisional application No. 61/727,817, filed on Nov. 19, 2012.

(51) Int. Cl.
*G01N 21/05* (2006.01)
*G01N 21/27* (2006.01)
(Continued)

(52) U.S. Cl.
CPC ........ *G01N 21/05* (2013.01); *B01L 3/502715* (2013.01); *B01L 3/502723* (2013.01);
(Continued)

(58) Field of Classification Search
CPC .................. G01N 21/05; G01N 21/27; G01N 2021/0346; B01L 3/502723; B01L 3/502784; C12Q 1/6806
See application file for complete search history.

(56) References Cited

U.S. PATENT DOCUMENTS 7,745,221 B2 * 6/2010 Butler ............... B01L 3/502761
422/504
8,557,518 B2 * 10/2013 Jovanovich ............ B82Y 30/00
422/502
(Continued)

OTHER PUBLICATIONS

International Search Report and Written Opinion under date of mailing of Mar. 6, 2014, in connection with PCT/US2013/070555.

*Primary Examiner* — Sang Nguyen
(74) *Attorney, Agent, or Firm* — Yakov S. Sidorin; Quarles & Brady LLP (57) ABSTRACT

Microfluidic cuvettes and a network of multiplexed channels including such cuvettes. The channels operationally share a main output channel defining an output of the network. A microfluidic channel includes an inlet, a cuvette, and an outlet that is coupled into the main output channel. The network is configured to provide a difference in resistances, to the fluid, by the main output channel and by an individual outlet is sufficient to prevent cross-contamination of different cuvettes, thereby operably isolating individual channels from one another. An individual cuvette is adapted to substantially prevent the formation of air-bubbles as part of the fluid flow through the cuvette and, therefore, to be fully (Continued)

filled and fully emptied. A system and method for photometric measurements of multiple fluid samples employing such network of channels.

8 Claims, 7 Drawing Sheets

(51) Int. Cl.
    *G01N 21/03*     (2006.01)
    *B01L 3/00*     (2006.01)
(52) U.S. Cl.
    CPC ........ *B01L 3/502746* (2013.01); *G01N 21/03* (2013.01); *G01N 21/27* (2013.01); *B01L 2200/027* (2013.01); *B01L 2200/0684* (2013.01); *B01L 2200/141* (2013.01); *B01L 2300/0851* (2013.01); *B01L 2300/0858* (2013.01); *G01N 2021/0346* (2013.01); *G01N 2021/0378* (2013.01); *G01N 2021/054* (2013.01)

(56) References Cited

U.S. PATENT DOCUMENTS

| | | | |
|---|---|---|---|
| 9,211,539 B2* | 12/2015 | Amin | B01F 5/102 |
| 2002/0097632 A1 | 7/2002 | Kellogg et al. | |
| 2005/0105077 A1* | 5/2005 | Padmanabhan | G01N 15/1484 356/39 |
| 2007/0003434 A1 | 1/2007 | Padmanabhan et al. | |
| 2007/0014695 A1* | 1/2007 | Yue | B01L 3/502707 422/400 |
| 2007/0280857 A1* | 12/2007 | Song | B01L 3/502723 422/400 |
| 2008/0118369 A1* | 5/2008 | Sando | B01L 3/50273 417/36 |
| 2008/0273918 A1 | 11/2008 | Linder et al. | |
| 2009/0051901 A1 | 2/2009 | Shen et al. | |
| 2012/0309648 A1* | 12/2012 | Tseng | B01F 5/102 506/11 |
| 2014/0141438 A1* | 5/2014 | Song | B01L 3/502723 435/6.12 |

* cited by examiner

SYSTEM AND METHOD FOR INTEGRATED MULTIPLEXED PHOTOMETRY MODULE

CROSS-REFERENCE TO RELATED APPLICATIONS

This application represents the national stage entry of PCT International Application No. PCT/US2013/070555 filed Nov. 18, 2013, which claims the benefit of, U.S. Provisional Patent Application No. 61/727,817 filed on Nov. 19, 2012, the disclosures of which are incorporated by reference here in their entirety for all purposes.

TECHNICAL FIELD

The present invention relates generally to systems and methods for conducting chemical, biochemical, and/or biological assays on a sample and, more particularly, to multiplexed optical spectroscopy performed on samples in microfluidic chambers.

BACKGROUND

Microfluidic devices and systems comprising such devices employ small capillaries or microchannels or cuvettes associated or even integrated with a solid substrate to perform a variety of operations in analytical chemical and biochemical applications on a very small scale. The small size of these systems allows for increased reaction rates that use less reagent volume and that take up far less laboratory or industrial space. Microfluidic systems thus offer the potential for attractive efficiency gains, and consequently, substantial economic advantages.

A variety of spectroscopic techniques can be employed in conjunction with microfluidic devices, including those utilizing infrared (IR) radiation, visible light, and/or ultraviolet (UV) radiation, and light-scattering spectroscopy, for example. In research or industrial settings, microfluidic devices are typically employed in biochemical or cell-based assays that use spectroscopic detection systems to quantify labeled or unlabeled molecules of interest. Microfluidic devices generally employ networks of integrated microscale channels and reservoirs with the use of which fluid samples materials are transported, mixed, separated and detected, and various optical systems that are embedded or externally arranged for recognition, detection, quantification, as well as other manipulations of the fluidic samples.

There exists a need in expansion of assay menu capacity of a microfluidic photometric system that would manifest in reduction of volume of a liquid sample required for the measurement and improving the accuracy and precision of the photometric measurement. Point of care integrated blood analysis instruments and environmental monitoring instruments are but two examples of devices that would benefit from such expansion.

SUMMARY OF THE INVENTION

Embodiments of the present invention provide a chip containing a microfluidic delivery channel having an inlet portion and an outlet portion and a cuvette portion therebetween in fluid communication with the inlet and outlet portions, said microfluidic delivery channel dimensioned to prevent formation of an air-bubble therein when a fluid is flowing along the channel. Accordingly, the microfluidic channel of the invention is operable to be substantially completely filled and substantially completely emptied. The cuvette portion includes a wall and a bottom, the wall being generally transverse to the bottom. The cuvette portion of the network may define a substantially circular projection onto a surface of the chip. The chip may additionally include a transition channeling portion fluidly connecting at least one of an inlet portion and a corresponding cuvette portion and an outlet portion and a corresponding cuvette portion. Such transition portion has a length and characterized by a cross-sectional area that is bigger than a cross-sectional area of a respectively corresponding a least one of inlet and outlet portions. In one implementation, the microfluidic delivery channel is dimensioned such as to prevent formation of an air-bubble therein when a fluid is flowing along said microfluidic channel.

Embodiments further provide a microfluidic component or chip carrying a network of microfluidic delivery channels, each channel having an inlet portion, an outlet portion, and a cuvette portion between the inlet and outlet portions in fluid communication therewith. The microfluidic component further carries a main outlet channel having an end, the main outlet channel configured in fluid communication with each outlet portion such as to provide a flow of the sample in a first direction from an inlet portion through a corresponding microfluidic delivery channel to the end of the main outlet channel and prevent a flow of the sample in a second direction from the main channel into the corresponding microfluidic delivery channel. In one embodiment, the network of microfluidic channels is structured such that each first microfluidic delivery channel disposed on one side of the main outlet channel has a corresponding second microfluidic delivery channel disposed on the other side of the main outlet channel and, in a specific implementation, the network may be structure symmetrically with respect to the main outlet channel. In a related implementation of the network, a first outlet portion and a second outlet portion are connected to the main output channel at first and second points along the main output channel, and, in addition, any of the first and second outlet portions is configured to define a first level of resistance to a fluid flowing therethrough towards the main outlet channel, and a segment of the main outlet channel defined between the first and second points is configured to define a second level of resistance to the fluid flowing therethrough towards the end, such that the first level of resistance being at least 200 higher than the second level of resistance.

Embodiments further provide a system for photometric measurements including the above-described network of microfluidic channels and further including an array of photodetectors and array of light sources positioned to sandwich the chip carrying the network between these two arrays with each cuvette portion oriented to transmit light from a corresponding light source to a corresponding photodetector.

Embodiments additionally provide a method for performing a photometric measurement. Such method includes (i) transmitting light from a first light source to a first photodetector through a corresponding first cuvette containing a first fluid sample delivered to the first cuvette from a corresponding first inlet channel; and (in transmitting light from a second light source to a second photodetector through a corresponding second cuvette containing a second fluid sample delivered to the second cuvette from a corresponding second inlet channel; wherein the first and second cuvettes are dimensioned to substantially prevent a formation of air-pockets therein while first and second fluid samples flow therethrough. The method further includes acquiring data representing the first and second fluids and removing the first and second fluids from the corresponding first and second cuvettes through respectively corresponding first and second outlet channels to a main output channel. Additionally or in the alternative, the method is made operable when each of the first and second cuvettes includes a corresponding wall and a corresponding bottom, the wall being inclined with respect to the bottom at an obtuse angle. The step of removing the fluids from the cuvettes may email removing a fluid from a cuvette through a corresponding outlet channel to a main output channel dimensioned to provide a first resistance, to the fluid flowing therethrough, that is at least 200 times larger than a second resistance provided to the fluid flowing through the outlet channel.

BRIEF DESCRIPTION OF THE DRAWINGS

The invention will be more fully understood by referring to the following Detailed Description in conjunction with the Drawings.

DETAILED DESCRIPTION

In accordance with an idea s of the present invention, a microfluidic cuvette component is disclosed that is structured such as to be substantially completely filled and emptied, in operation, without leaving an unused volume of the cuvette. Implementations of such cuvettes are many, including, for example, sample metering and or conditioning. In this case, the cuvettes (also referred to as chambers) are used to isolate a repeatable well defined volume of sample for further downstream processing by, for example, appropriately incorporating fluidic valves up-stream and down-stream with respect to the chambers to isolate the sample prior to processing. In another application, referred to herein as "volume sensing", an individual cuvette or chamber that is adapted to be filled and emptied substantially completely is used to determine when a particular volume of fluid has been introduced into the system. Such volumes sensor could be placed at the outlet of the cuvette or chamber such that when chamber is filled, the sensor is triggered generating an indicator that the target volume has been reached.

While the proposed cuvette element is operable and usable on its own, a fluidic network containing such fully fillable-and-emptied cuvettes is also implemented. The network is adapted to operationally isolate the individual cuvettes contained in different branches of the network, is also implemented for use different applications including, for example, drug screening, facilitation of multi-reagent chemical reactions, and photometric measurements. In the case of drug screening for example, the proposed fluidic network is adapted to differentiate among individual cell cultures multiplexed cell culture sample. An example of the fluidic network employs an array of cell culture chambers that can be individually stimulated with different chemicals but share a common outlet. So designed network is configured to prevent cross-talk between the chambers keeping each one in isolation. In another implementation, the proposed fluidic network facilitates multi-reagent chemical reaction processes by isolating different components of a chemical reaction from one another. When different branches of the fluidic network are flushed, the reaction would be initiated only in the common waste stream. In this manner, the order in which reagents are added to the reaction solution are controlled, thereby facilitating the control over the reaction products.

An example of a microfluidic photometric apparatus is also disclosed that takes advantage, in operation, of an individual cuvette and/or of the proposed fluidic network. An implementation of the photometric apparatus has a multiplexed cuvette unit that is structured for repeatable and volumetrically uniform fill-measure-flush-and-re-use operation substantially without forming air bubbles in the cuvette while, at the same time, providing sample aliquots with geometrical constraints defined in such a fashion as to ensure that a pathlength of light traversing the cuvette installed in the photometric apparatus is substantially invariant.

References throughout this specification to "one embodiment," "an embodiment," "a related embodiment." or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and/or in reference to a figure, is intended to provide a complete description of all features of the invention.

In addition, in drawings, with reference to which the following disclosure may describe features of the invention, like numbers represent the same or similar elements wherever possible. In the drawings, the depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and not all, features of the invention. A given drawing and an associated portion of the disclosure containing a description referencing such drawing do not, generally, contain all elements of a particular view or all features that can be presented is this view in order to simplify the given drawing and the discussion, and to direct the discussion to particular elements that are featured in this drawing.

A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described features, structures, or characteristics of the invention may be combined in any suitable manner in one or more embodiments.

Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown.

The invention as recited in the appended claims is intended to be assessed in light of the disclosure as a whole.

Photometric and radiometric methodologies (aggregately referred to, for the purposes of this disclosure, using such terms as "photometry" and "photometric") have been widely adopted as tools for determining concentrations of analytes in both human and animal biological samples such as, for example, blood, urine, and saliva, to name just a few. (Photometric methods can also be used for environmental testing. For instance, groundwater can be tested for contamination due to various chemical species.) In vitro diagnostic devices using photometric detection techniques have been developed for a large variety of clinical biomarkers. In general, there are three classes of reaction schemes for clinical assays that are evaluated using photometric methods.

Chemical endpoint reactions involve the complete conversion of an analyte using synthetic chemicals. The conversion results in a change in absorbance of the sample, which is measured after the reaction has completed. The final absorbance of the sample is proportional to the analyte concentration. Some analytes, the concentrations of which are determined with chemical endpoint assays, include hemoglobin, calcium, and total protein.

Enzymatic endpoint reactions also involve the complete conversion of an analyte, such as glucose, for example. However in this case, the conversion is catalyzed by the presence of an enzyme. The absorbance of the sample is, again, measured after the reaction is completed and is proportional to the analyte concentration. Analytes the concentrations of which are determined with enzymatic endpoint reactions include creatinine, glucose, and bilirubin.

Enzymatic rate reactions involve the continuous conversion of an analyte catalyzed by an enzyme. Absorbance of a sample in this case is monitored over time, and the rate of change of absorbance is proportional to the concentration of an analyte. Enzymatic rate reactions normally require tight temperature control to ensure that the reaction rate remains constant over the course of the measurement. Analytes the concentrations of which are determined with enzymatic rate reactions include alkaline phosphatase (ALP), alanine aminotransferase (ALT), and chloride.

Based on Beer's law, according to which the absorption of light in a sample is proportional to the concentration of the analyte, the absorbance of light $A_X^\lambda$ at wavelength $\lambda$, caused by the presence of species X at a concentration [X] along a path L through the sample, can be expressed as $$A_X^\lambda = \varepsilon_X^\lambda [X] L = \log_{10}\left[\frac{I_0}{I}\right] \qquad \text{Eq. (1)}$$

where $\epsilon_X^\lambda$ is the millimolar absorptivity of the species X at the designated wavelength. Accordingly, the concentration of the sought-after species can be expressed as $$[X] = \log_{10}\left[\frac{I_0}{I}\right] / (\varepsilon_X^\lambda L) \qquad \text{Eq. (2)}$$

The transmitted through the sample radiant power is determined by integrating the light intensity transmitted by the sample over a range of wavelengths of interest and multiplying by the sensitivity of the detector at those wavelengths. This can be accomplished in several ways. A broad spectrum light source may be used with a spectrophotometer as a detector which splits the transmitted light into component wavelengths that are individually detected and can be read at the wavelengths of interest. Alternatively, a narrow band wavelength light source may be used with a single point detector to absorb all of the transmitted light.

Generally, the terms "sample", "biological sample", "chemical sample" and the like as used herein refer to a sample of fluid material that is assumed to contain an analyte of interest. For example, samples include various fluids such as various solutions, bodily fluids (such as whole blood, serum, plasma, cerebrospinal fluid, urine, lymph fluids), and other fluids (such as, for example, cell culture suspensions, cell extracts, cell culture supernatants). A sample may be suspended or dissolved in, for example, buffers, extractants, solvents, and the like. Additional examples of samples are provided by fluids deliberately created for the study of biological processes or discovery or screening of drug candidates. The latter include, but are not limited to, aqueous samples that have been doped with bacteria, viruses, DNA, polypeptides, natural or recombinant proteins, metal ions, or drug candidates and their mixtures.

Conventionally, to conduct optical spectroscopic and/or photometric analysis, a sample should be placed in a cuvette that is used and replaced after the measurement is complete. The currently employed microfluidic cuvettes possess shortcoming that substantially limit their application in a multiplexed photometric system.

Indeed, in a multiplexed microfluidic photometric system adapted to perform parallel photometry measurements on multiple, generally different analytes, a cuvette volume is an important figures of merit. The smaller the volume of a cuvette, the higher the degree of system and measurement multiplexing is possible for a given "footprint" of the device and the smaller the required sample volume. In order to make measurements of the sample reproducible, a cuvette must have a very well-defined thickness or length (which translates to a well-defined sample path length through the cuvette). The path length of the cuvette determines the measurable concentration of an analyte for the instrument. Accordingly, there is a need for a cuvette that is configured to ensure that the corresponding sample path length accommodates the entire range of concentrations of interest.

In addition, a microfluidic cuvette must be configured such that, in operation, it is completely filled with the sample at hand without introducing air bubbles that obscure the optical path of light used for photometric measurements. Air in the path of light leads to light diffraction, thereby causing errors in measurement of light absorbance.

Moreover, a cuvette is desired that lends itself to being re-used—in contradistinction with replaceable cuvettes of the related art devices—and, therefore, "flushed" to entirely to remove any trace of the sample once a measurement has been made. The latter requirement arises from a need to ensure that no sample-carryover contamination occurs from one measurement to the next.

The present invention stems from the realization that the above-mentioned industrial needs are addressed with a microfluidic device configured to include a multiplicity of unidirectional-flux cuvettes that share a common fluidic outlet, are devoid of valves, are dimensioned to substantially eliminate air-bubble formation in a flow of fluid through each of the cuvettes, and that are subject to positive pressure facilitating substantially complete removal of the sample residue and, therefore, use and reuse of the same microfluidic chip.

Figure 1A:
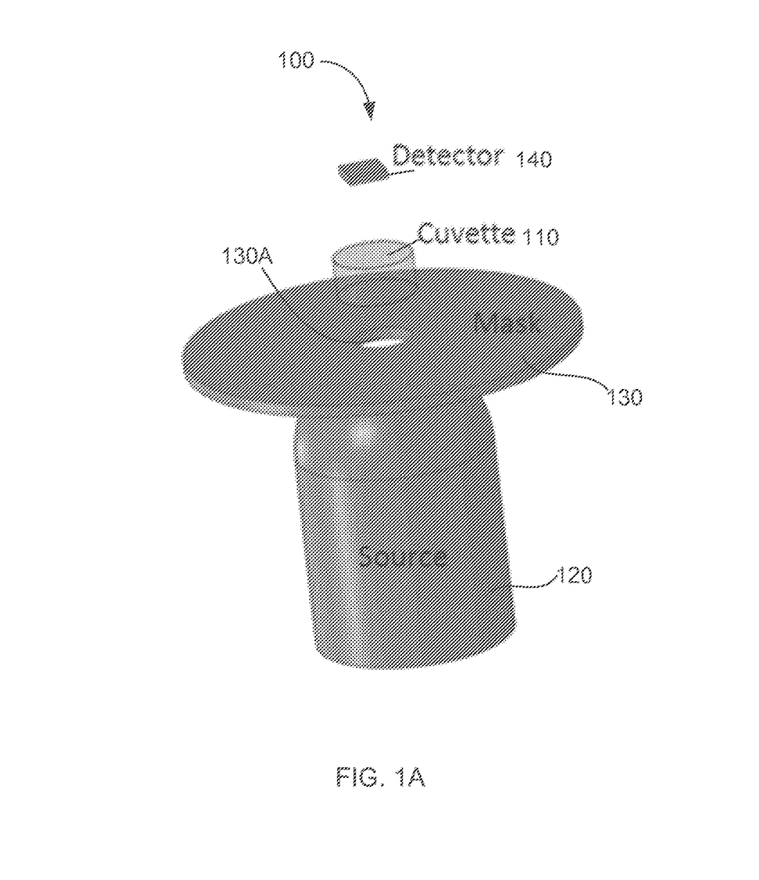
FIGS. 1A and 1B are perspective and plan view illustrations of a simplified photometric microfluidic system employing a single cuvette.
Figure 1B:
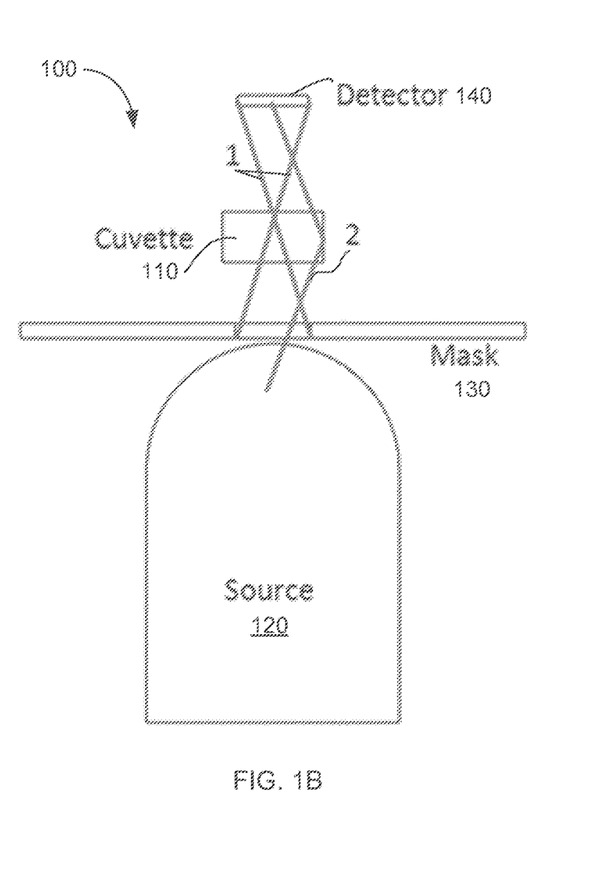

FIGS. 1A and 1B provide perspective and plan view illustrations of a simplified photometric microfluidic system 100 employing a single cuvette 110, providing a conveyor or container for a fluid sample (not shown) that is interrogated with light emanating from the light source 120. Light from the source 120 passes through a spatial mask 130 having an aperture 130A. In reference to FIG. 1A, light propagating between the source of light 120 and the cuvette 110 along path 1 is transmitted directly through the aperture 130A on its way to a detector 140, while light following path 2 is shown to interact with (reflect off of) a side of the cuvette 110. In one implementation, the source of light 120 includes a 5 mm diameter LED, the opening 130A of the approximately 0.3 mm thick mask 130 has a diameter of about 1.5 mm, a chamber of the cuvette 110 has a diameter of about 2 mm and thickness of about 1 mm, while the area of the detector 140 is about 1 mm².

Figure 2:
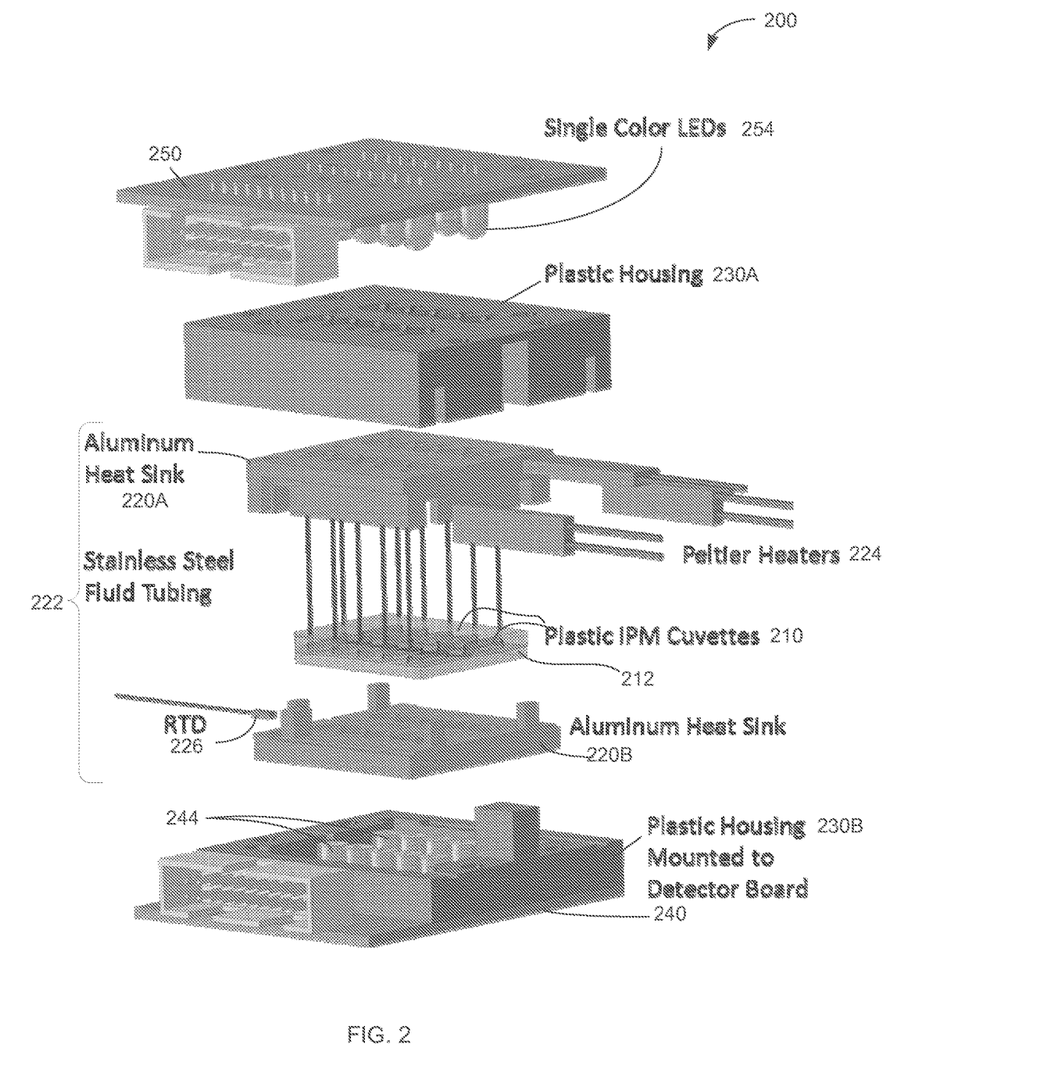
FIG. 2 is an exploded perspective view of an embodiment of the integrated photometric module of the invention.

As another preliminary matter, FIG. 2 provides an exploded perspective view of a simplified embodiment of a photometry module (IPM) according to an embodiment 200 of the invention that employs a multiplicity of individually addressable cuvettes 210 (at least some of which may be similar to the cuvette 110 of FIGS. 1A, 1B). The cuvettes 210, configured for multiplexed photometry measurements, are disposed in association with a polymeric chip 212 and share a common waste outlet, while each of the individual cuvettes 210 includes a circularly-shaped chamber, as discussed in detail below. The IPM cuvette-chip 212 is housed in association with an aluminum housing 220A, 220B that is used as a heat sink to maintain a constant temperature of the system. The system 222 (including the chip 212 and the sink elements 220A, 220B) is heated with Peltier heaters 224 located, as shown, around the exterior of the aluminum heat sink housing 220A, 220B. The temperature of the system is monitored with a resistance temperature detector 226 (RTD) located within the bounds of the heat sink 220A, 220B in contact with the polymeric chip 212. A feedback control loop (not shown) is employed to maintain the system at a constant temperature.

The heat sink 220A, 220B (with all the enclosure thereof) is disposed inside a plastic housing 230A, 230B configured to insulate the system from the environment. A circuit board 240 containing an array of photodiodes 244 (such as, for example, an array of individual single-point photodiodes in T 1¾ packages) is mounted on one side of the plastic housing. In one implementation, the number N of photodiodes equals that of the cuvettes 210. The photodiodes may have, for example, square detectors with active areas of about 1 mm×1 mm and be protected by flat optical windows. A complementary circuit board 250 containing a corresponding number N of narrow-band (or substantially single-wavelength) LEDs 254 in T 1¾ packages with lensed tops is mounted on the other side of the plastic housing 230A.

As an option, a spatial mask (such as the mask 130 of FIGS. 1A, 1B, for example) can be used to limit the area of light incident on the detectors 244 from the light source 254 through the cuvettes 210. In one embodiment, a substantially opaque at the wavelength(s) of interest mask layer can be sandwiched between the cuvette chip 112 and the aluminum heat sink portion 220A such as to have the apertures spatially aligned with the individual cuvettes 210.

Optimization of a Single-Cuvette-and-Channel Geometry

It is appreciated that optimization of the operation of a microfluidic system depends, at least in part, on the ability of a user to utilize a sample of a limited volume. To achieve such optimized operation, the volume of the cuvette should not contain 'dead space' that is filled with the substance of the sample but is not taking part in a photometric measurement. The required operational footprint of the cuvette, which facilitates elimination of such 'dead space', relates to the area of the photodetector used for photometric measurements. In other words, the cuvette should be dimensioned such that every portion of light collected by the photodetector has passed through the cuvette and that path length of such light through the cuvette is substantially the same for any portion of the collected light. If this condition is not observed, the background noise associated with the measurement is increased and the measurements system will have reduced sensitivity at the lower end of the sample-concentration range.

Another factor restricting configuration of a photometric system is a path length, for light propagating from a source of light through the sample being measured to a detector. Typical microfluidic photometric systems are structured to ensure that such path length is on the order of 1 cm. Some point-of-care blood analysis instruments, however, may be configured to utilize path lengths as small as a few hundred microns.

In further reference to FIG. 2, the entire operational volume $V_{sys}$ of a multiplexed photometric system is calculated as $$V_{SYS} = NAL + V_C \qquad \text{Eq. (3),}$$

where N is the number of cuvettes 210, A is the required area (footprint) of a single cuvette, L is the thickness of a single cuvette, and $V_C$ is the volume of a network of channels adapted to provide feeding of the sample to the cuvettes 210 and removal of the waste from the cuvettes (and referred to as feeder-waste channel network, for simplicity). The concentration of a diluted sample is given by $$[X] = [X]_S (1+D) \qquad \text{Eq. (4),}$$

Where the concentration of an undiluted sample is $[X]_S$ and the dilution ratio of the sample assay is defined as D. Based on Eqs. (1) and (4), $$A_X^\lambda = \epsilon_X^\lambda [X]_1 L_1 = \epsilon_X^\lambda [X]_2 L_2 \qquad \text{Eq. (5A)}$$

$$[X]_2=[X]_1(L_1/L_2) \quad \text{Eq. (5B)}$$

and, in order to maintain a value of sample absorbance that remains invariant as the cuvette thickness changes, the dilution ratio D must also change as a function of the thickness of the cuvette:

$$D_2=(L_2/L_1)(1+D_1)-1 \quad \text{Eq. (6)}$$

If the overall operational volume of the system is equal to the volume of the diluted sample, the volume $V_S$ of the undiluted sample corresponding to the entire operational volume $V_{sys}$ is determined as $$V_{SYS}=V_S(1+D) \quad \text{Eq. (7)}$$

Assuming that a pathlength of light and the sample dilution ratio, corresponding to a chosen reference measurement method, are $L_R$ and $D_R$, respectively, the required volume $V_S$ of the undiluted sample is determined, from Eqs. (3), (5A, 5B), (6), and (7), to be reciprocal to the cuvette thickness L:

$$V_S=L_R(NAL+V_C)/(L+LD_R) \quad \text{Eq. (8)}$$

Overall, the minimum operational value of the cuvette thickness is determined both by the necessity to measure the lowest concentration analyte (at the dilution ratio of the assay) and by the availability of the sample to be measure. As the cuvette thickness decreases, the necessary sample dilution ratio for an assay decreases. If the dilution ratio of the sample is too low, there may not be enough volume of sample to fill a multiplexed cuvette system.

Geometry of an entrance portion of the microfluidic network (for example, a feeder channel that leads to the cuvette) and that of an exit portion of the network (a waste channel following the cuvette) are additional factors defining the efficiency of operation of the microfluidic system.

In reference to FIGS. 3A, 3B, 4A, and 4B, to ensure that no air bubbles are trapped and/or present in a cuvette filled with the substance of the sample and that the fluid flowing through the cuvette maintains a continuous streamline along the wall, a surface defining a wall of the cuvette must be sufficiently smooth and define a tangent described by a continuous function. In a specific embodiment, a wall of the cuvette is defined by a surface that is differentiable (that is, has a derivative) at any point along the wall.

Figure 3A:
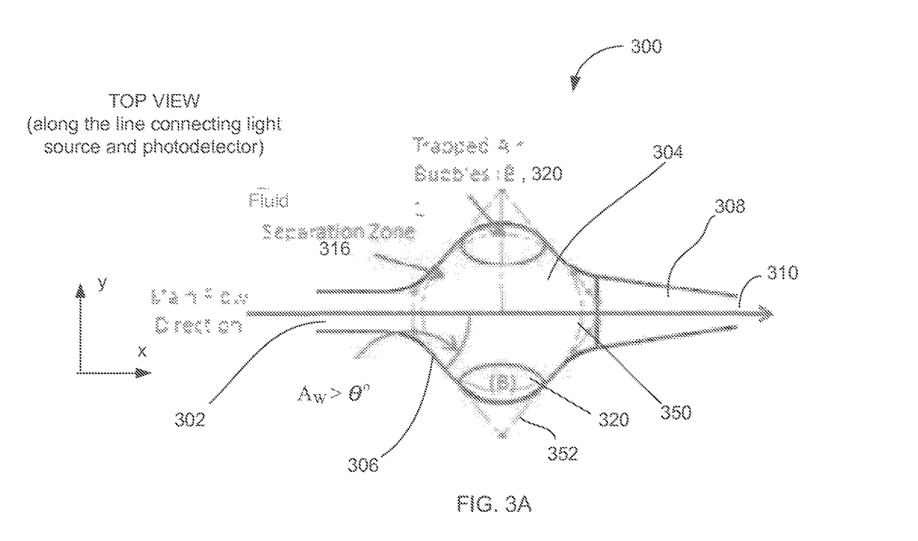
FIGS. 3A and 3B are views of an embodiment the configuration of which facilitates formation of air-bubbles inside a microfluidic cuvette.
Figure 3B:
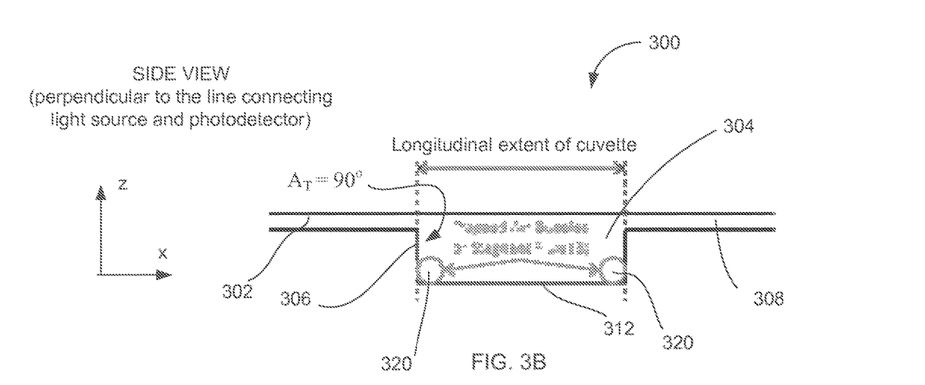
Figure 4A:
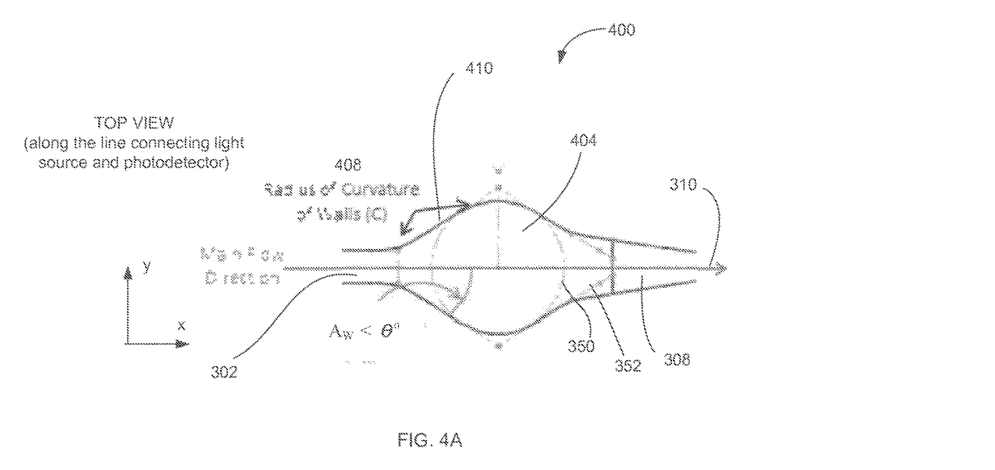
FIGS. 4A and 4B are views of an embodiment which is configured to minimize air-bubble formation.
Figure 4B:
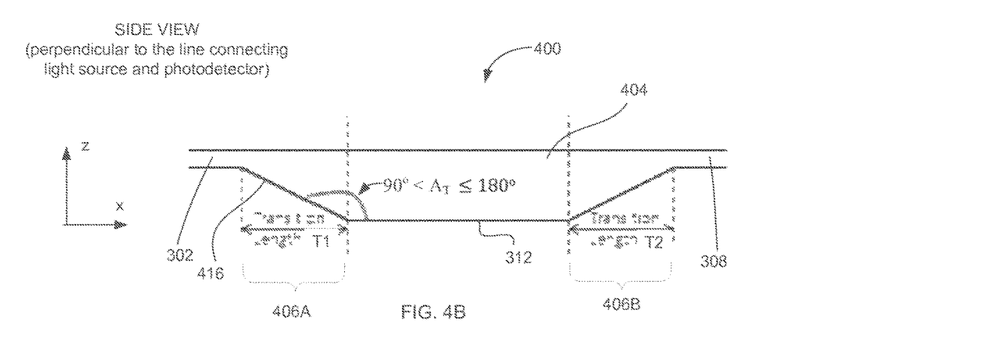

FIGS. 3A and 3B illustrate, not to scale, top and side views, respectively, of an embodiment 300 of a microfluidic network portion including a feeder channel 302, a cuvette 304 with a wall 306, and a waste channel 308. In order to reduce the 'dead' volume, the fluidic channels that feed and empty the cuvette should be as small as possible. The cuvette 304 has an approximately rectangular profile defined by a substantially step-like transitions between a chamber of the cuvette 304 and the feeder/waste channels 302, 308 in a cross-sectional plane that is parallel to both the main direction 310 of fluid sample flow and the direction of propagation of light (shown as axis z in FIG. 3B). In particular, the transition angle $A_T$ between the wall 306 and the bottom 312 of the cuvette 302 is substantially 90°. In contradistinction to the embodiment of FIGS. 3A, 3B. FIGS. 4A and 4B illustrate an embodiment 400 the corresponding transitional angle $A_T$ of which, defined by a non-zero-length $T_1$ transition between the feeder channel 302 and the bottom 312 of the cuvette, is obtuse to define a ramp-surface or wall 416, inclined with respect to the bottom surface 312. Accordingly, the transition between the feeder or inlet channel 302 and the cuvette 404 includes a entrance ramp region 406A. In one implementation, a minimum transition angle $A_T$ of about 144° between a wall in transition region and the bottom of the cuvette ensures that neither bubbles nor stagnant fluid are trapped in the corners and/or by the edges of the cuvette 404. (the upper limit for this transition angle is, understandably, 180 degrees.) Similarly, the embodiment 400 can be adapted to contain an optional exit ramp region 406B, the transition length of which is denoted $T_2$ and which has a corresponding transition angle (not shown in FIG. 4B)

It is appreciated that the smaller the microfluidic channels of the device, the more such channels are susceptible to clogging with the substance of the sample being measured.

In either of FIGS. 3A and 4A, the circular dashed line 350 identified the area or footprint, of the corresponding cuvette 304, 404, that is required to ensure that all light leaving the source and reaching the detector has passed through the cuvette (and thus the sample). The dashed line 352 defines a parallelogram corresponding to tangents to fluidic cuvette walls.

According to an embodiment of the invention, the spatial rate of widening of the microfluidic network at the entrance of the cuvette, at the transition region between the inlet portion and the cuvette, is sufficiently low to ensure that the fluid sample proximate to the wall of the cuvette doesn't separate from the wall and form bubbles near the edges of the cuvette. For example, the fluid sample may be controlled using a boundary layer or surface tension effects. This spatial rate of widening of the transition portion is defined, for example, by an angle of widening $A_W$ formed by a wall in the transition region with respect to an axis of at least one of the inlet and outlet portions; the value of $A_W$ is smaller than a threshold angle value θ. If, as illustrated in FIG. 3A, such angle $A_W$ between the wall 306 and the direction of the flow 310 exceeds the operationally corresponding threshold value θ, the nature of interaction between the fluid stream in the separation zone 316 and the wall 306 is likely to promote formation of the bubbles 320 (region B in FIG. 3A) in the cuvette 304B. In contradistinction with the embodiment of FIGS. 3A and 3B, the embodiment of FIGS. 4A and 4B, having a cuvette 404 that is characterized by $A_W<θ$, does not promote formation of the bubbles. In one embodiment, the value of the threshold angle θ is about 36 degrees and, therefore, $0 \leq A_W \leq 36°$. In another embodiment, the value of the threshold angle is about 30 degrees and $0 \leq A_W \leq 30°$, and in an alternative embodiment the value of the threshold angle is about 25 degrees and $0 \leq A_W \leq 25°$. In a specific case when $A_W \sim 0°$ and the depth of the feeder channel 302 approximately equals to the depth of the cuvette 304, 404 (not shown), there is substantially no potential for trapping air bubbles or leaving stagnant fluid at the bottom of the cuvette.

Furthermore, an embodiment of the IPM of the invention (such as the IPM 200 of FIG. 2, for example) is optionally equipped with a unit providing a positive air flow through the microfluidic network including the cuvettes 210, and each of the cuvettes 210 is adapted to ensure that there are no 'stagnant' areas in the cuvette in which the residue of the fluid sample remain after the cuvette has been flushed with air. Accordingly, and in further reference to FIGS. 4A, 4B, the radius 408 of curvature defined by a cuvette wall 410 in a cross-sectional plane that contains the axis 310 of fluid flow and that is substantially normal to the optical axis (locally defined as z-axis) should be maximized. In one example, where the footprint of the cuvette of about 2 mm (as defined by the dashed circle 350) implies a maximum radius of curvature of about 1 mm for the channel walls in the middle of the cuvette region (approximately at a midpoint between the inlet 302 and outlet 308 of the cuvette). Optimization of a Multiple-Cuvette-and-Channel Multiplexed Geometry Embodiments of the invention employ reusable microfluidic chips or elements that combine, in a spatially multiplexed fashion, multiple individual cuvettes each of which is adapted for a designated unique type of measurement. For example, multiple individual cuvettes on the same chip may be used for contemporaneous measurements of the same type of sample the concentration of which is different in different cuvettes. In a related example, multiple individual cuvettes on the same chip may be used for contemporaneous measurements of samples of different types or nature (for example, samples containing different analytes). In either case, to use the smallest possible volume of a sample in an individual cuvette, the 'dead' volume of such cuvette is minimized, as mentioned above. A person of skill in the art will appreciate that the required operational independence of the individual but structurally-multiplexed cuvettes from one another begs a question of how to preclude different sample aliquots in different individual cuvettes from mixing with one another and, by virtue of such mixing, introducing an error in the measurements. This requirement becomes even more stringent if another requirement is imposed to not remove the reusable microfluidic chip from the photometric apparatus between immediately sequential measurement.

Put differently, the complexity of these problems can be phrased as achieving the operational multiplexing of cleanable cuvettes on the same (optionally non-removable from the photometric apparatus) chip, while (i) minimizing the number of necessary fluidic connections on the chip, to reduce the overall footprint of the chip and the 'dead' volume of the cuvettes and (ii) ensuring that samples in individual cuvettes are substantially isolated from one another. According to an embodiment of the invention, a solution to this complex of problems is provided by merging the individual outlet channels of individual cuvettes into a common outlet for the overall multiplexed system of cuvettes. The following discussion is provided in reference to FIG. 5 providing a diagram of an embodiment 500 of a multiplexed microfluidic chip for use with an embodiment of the photometric apparatus of the invention.

Sample Isolation.

The embodiment 500 shows an example of multiplexing of individual microfluidic elements each of which includes a corresponding input channel or inlet 502(*a, b, c, d, e, f, g, h, i, j*), a cuvette 504(*a, b, c, d, e, f, g, h, i, j*), and a corresponding individual output or outlet 508(*a, b, c, d, e, f, g, h, i, j*). For simplicity of illustration, only some of the above-mentioned elements are labeled in FIG. 5. The individual inlets 502*a* through 502*j* serve a purpose of operational isolation of individual cuvettes 504*a* through 504*j* so that different samples in these cuvettes do not contaminate one another. For simplicity of the fluidic manifold that will distribute and return samples, the individual outlets 508*a* through 508*j* are merged to and share a common chip outlet 516. To operationally isolate the samples in the cuvettes 504*a* through 504*j*, the fluidic resistance of the individual cuvette outlets 508*a* through 508*j* must be sufficient to ensure that pressurized fluid in the main outlet channel 516 flows out of the device (along the arrow 518) through the common outlet rather than back, up-the-stream through another cuvette (for example, through the outlet 508*a* towards the cuvette 504*a*). The fluidic path length corresponding to an individual outlet channel 508*a* through 508*j* must be sufficiently long to prevent diffusive mixing of the samples in individual cuvettes 504*a* through 504*j*.

Figure 5:
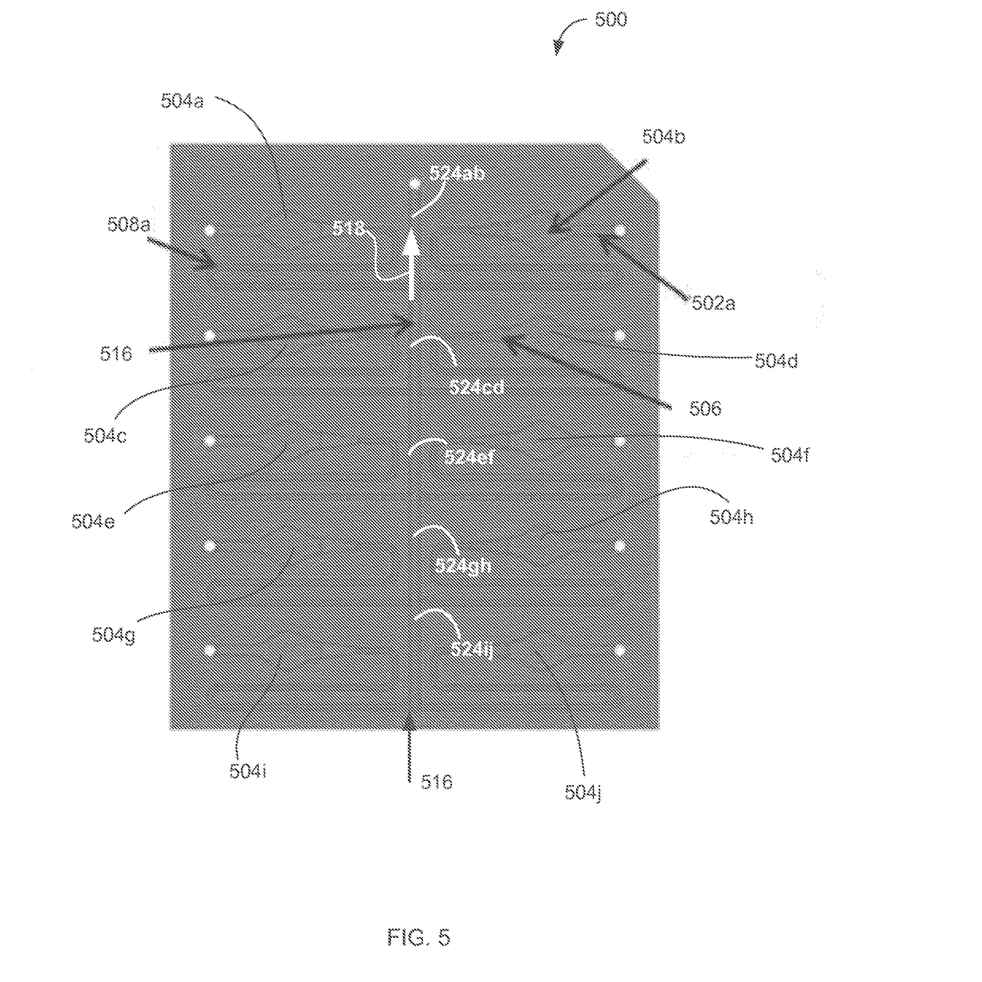
FIG. 5 is a diagram illustrating schematically an embodiment of a multiplexed fluidic network containing multiple cuvettes (each cuvette having corresponding inlets, high-resistance outlets) and a low-resistance main outlet channel.
Figure 6A:
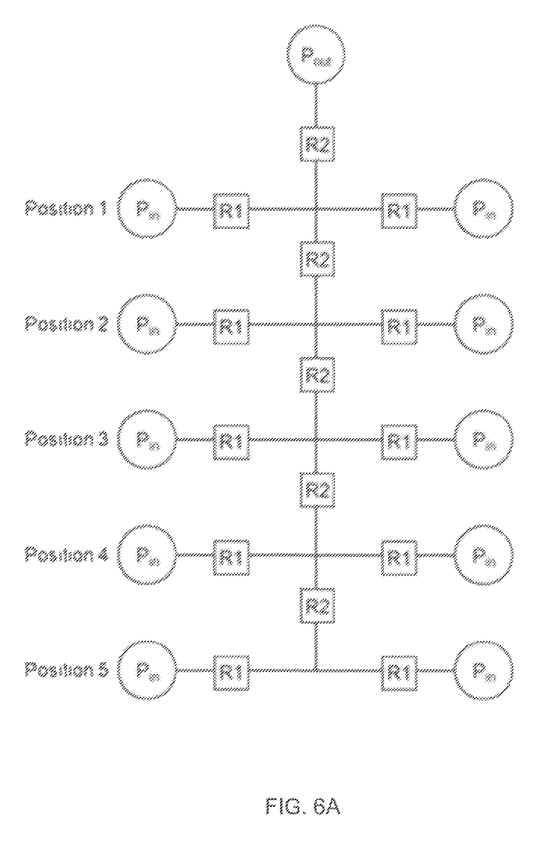
FIGS. 6A and 6B are diagrams illustrating the fluidic model representing the microfluidic network embodiment of FIG. 5.
Figure 6B:
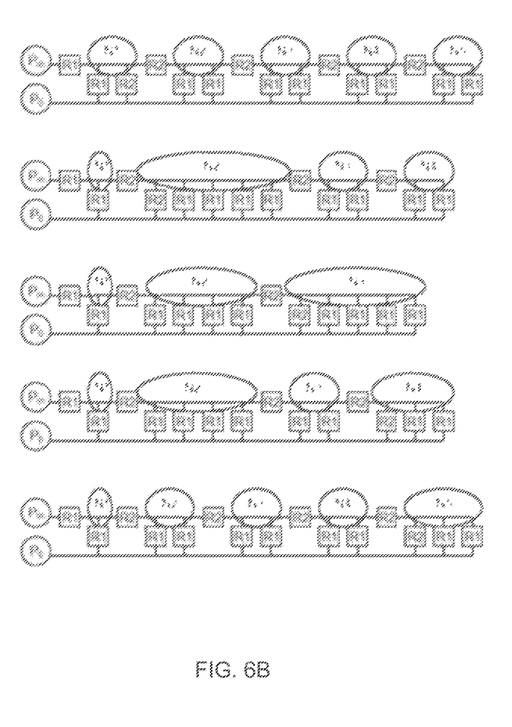

In reference to FIGS. 6A and 6B, showing examples of two schemes describing the fluidic model of the embodiment 500 of FIG. 5, the fluidic resistance R1 of the individual outlets 508*a* through 508*j* is, in one implementation, approximately 2 to 3 orders of magnitude higher than the resistance values R2 of segments 524*ab*, 524*cd*, 524*ef*, 524*gh*, and 524*ij*, of the main outlet channel 516, that are located between the cuvette pairs (504*a*, 504*b*), (504*c*, 504*d*), (504*e*, 504*f*), (504*g*, 504*h*), and (5041, 504*j*), respectively. In one implementation, the ratio of the resistance values R1/R2 is about a number of the individual cuvettes in the embodiment or higher. In different implementations, the ratio of resistance values R1 and R2 may range between about 200 and about 10,000. Furthermore, the entire measurement system, which includes the embodiment 500, is preferably a closed system with no air in any line in order to prevent residual flows. If there is any air in the system, it will compress during pressurization of the system and then when the system is de-pressurized, the air will expand causing residual flows which can lead to sample contamination. The nodes $N_i$ within the system of FIG. 6B represent the locations at which the fluidic pressure is approximately the same.

EXAMPLES

Figure 7:
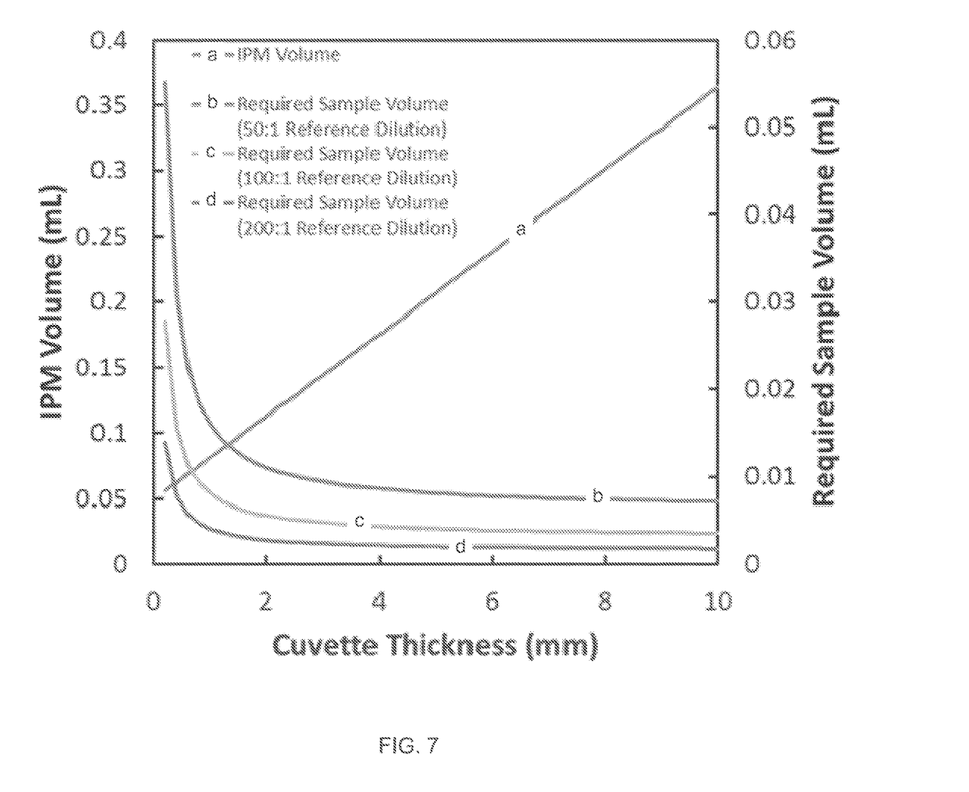
FIG. 7 is a plot representing dependencies of the IPM volume and the required volume $V_S$ of the undiluted sample on cuvette thickness, for several values of dilution ratio D.

In one implementation, and in further reference to FIGS. 2, 4A, 4B, and 5, an individual cuvette in a multiplexed chip 212, 500 used in the IPM 200 has a foot print defined by a circle with a diameter of about 2 mm. FIG. 7 is a plot showing a volume of the required undiluted sample as a function of the cuvette thickness and the reference dilution ratio, according to Eq. (8). According to FIG. 7, a cuvette with thickness of about 1 mm optimizes the reduction of the 'dead' volume of the overall microfluidic component system while maintaining, at the same time, an undiluted sample volume below about 0.02 mL. Therefore. FIG. 7 provides an illustration to an embodiment in which the operation of the multiplexed microfluidic chip 212, 500 is optimized for the cuvettes having thickness of about 1 mm. In the example of FIG. 7, the entrance channels (302, 502*a* through 502*j*) of the cuvettes (404, 504*a* through 504*j*) each have a depth of about 1 mm and a width of about 0.5 mm. The transition angle $A_7$ corresponding to the individual inlet transition area 406A is chosen to be about 180°, as discussed in reference to FIG. 4B. Each of the individual inlets (302, 502*a* through 502*j*) expands into the corresponding cuvette (404, 504*a* through 504*j*) at an angle $A_W$ of about 32°, as discussed in reference to FIG. 4A. The walls of an individual cuvette have a curvature radius 408 of about 1 mm. The individual exit channels (308, 508*a* through 508*j*) have a width of about 0.25 mm, a depth of about 0.05 mm, and a length of about 26 mm. The transition region 406B from an individual cuvette area to the corresponding exit channels (308, 508*a* through 508*j*) has a length $T_2$ of about 1.9 mm. The transition angle $A_T$ corresponding to the outlet transition region 406B is chosen to be about 153°. The main outlet channel 516 has a depth of about 0.25 mm and a width of about 0.5 mm. The distance between pairs of individual outlet channels along the length of the main outlet channel is about 5.4 mm.

In one implementation, and referring again to FIG. 2, the IPM 200 is operated as follows. The entire system is heated to about 37° C. (for example, for about 5 minutes) until a steady state is reached. Once the temperature of the system is stabilized, a dark reference voltage is measured for each detector 244 by determining the voltage corresponding to each detector when the respectively corresponding LED 254 is turned off. The IPM 200 is initially empty (contains air) prior to any measurement. Blank solutions are pre-loaded into a sample manifold (not shown in FIG. 2), which, in this example, contains ten slots for vials, one for each cuvette. The manifold is connected to the plastic cuvette with 3"-6" long rigid tubing (such as, for example, the one by PEEK, 1/32"OD, 0.015"ID) followed by 3"-6" long flexible tubing (such as that of Tygon, 0.06"OD, 0.02"ID). The manifold is pressurized to about 1 bar and the blank solutions flow into their respective cuvettes. The flow is stopped by venting the manifold to atmospheric pressure when liquid begins to flow out of the outlet tube (in one example, in about 5 to 15 seconds). The system is then closed by clamping the flexible tubing to ensure that there are no air pockets in the system (such as the head space in the manifold).

The transmission of light through the blank solution in a single cuvette is measured by turning on the LED 254, corresponding for that cuvette, waiting for a short period of time (such as 5 ms, for example), recording the voltage of the photodetector 244, turning off the LED 254, and waiting for another period of time (for example, 200 ms). This process is repeated three times and the average detector voltage for that cuvette is determined. The dark reference voltage for that detector is subtracted from the average voltage and the result is recorded. The process is repeated for each of the ten cuvettes in series.

Once the blank solutions have been measured, the sample vials are removed from the manifold and tubing is unclamped. The manifold is again pressurized to 1 bar and the system is flushed with air until all of the liquid is removed (for about 5 to 15 seconds). The samples are then loaded into the manifold in the same manner as the blank solutions.

The transmission of light through the samples is measured in the same manner as for the blank solutions. The absorbance of the samples is determined by calculating the logarithm of the ratio of the transmittance value corresponding to the blank solution to the transmittance value of the sample (corrected with the dark reference value, as already described).

For endpoint reactions, three measurements are taken for each sample and the averaged absorbance value is used to calculate the sample concentration. For rate reactions, the absorbance of the sample is continuously monitored (the system cycles through all of the cuvettes until stopped) and the rate of change of absorbance is used to determine the sample concentration.

The IPM embodiment 200 of FIG. 2, structured as described above in reference of FIG. 7, requires at least 0.02 mL of the fluid sample (for example, blood, serum, saliva diluted with reagent and/or buffer) to operate. In order to make accurate measurements of sample absorbance, the liquid sample in any given cuvette must not be contaminated by other samples. This means there can be no residual flows in the system. The tube clamping described in the previous section takes care of this requirement.

For enzymatic rate reactions, the sample and reagent are mixed outside the system at a temperature significantly lower than the chose steady-state temperature of operation (which, in the provided example, is about 37 C) in order to suppress the enzymatic rate reaction. When the sample is flown into the cuvette, it is warmed to 37 C as quickly as possible in order to make an accurate constant rate measurement. Assay chemistries for this system should preferably be adapted to be compatible with that process workflow.

In order to make accurate sample measurements, the LEDS 254 and corresponding electronic circuitry are configured to ensure that the output LED intensity does not drift over time. In particular, the duty cycles (on time/cycle time) of the operation of the LEDs 254 are chosen to be low enough to ensure that the LED intensity doesn't drift. In one example, the reported operation of 5 ms on/200 ms off satisfies this requirement for all of the LEDs currently used in the IPM system 200.

To effect the operation of an embodiment of the above-described IPM system (including the design of a multiplexed microfluidic chip according to the methodology described above) and performance of the steps required to acquire and process the photometric data representing results of the measurements of the fluid sample(s) passing through an individual cuvette of the IPM system may require the operation of a processor controlled by application-specific instructions stored in a tangible memory element. Those skilled in the art should readily appreciate that required algorithmical functions, operations, and decisions may be implemented as computer program instructions, software, hardware, firmware or combinations thereof. Those skilled in the art should also readily appreciate that instructions or programs defining the functions and elements of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

The disclosed embodiments of the invention discuss specific examples of isolation of multiple different sample chemistries within a single connected fluidic network, of design rules for optimizing physical characteristics of the measurement cuvettes and fluidic network, of design rules for cuvettes to be repeatedly used in a fluidic network (including sample loading without air bubbles and sample flushing without carryover contamination), and of performing simultaneous photometric measurements of (optionally multiple) samples at (optionally multiple) wavelengths in a consolidated package. Modifications to, and variations of, the illustrated embodiments may be made without departing from the inventive concepts disclosed herein. Furthermore, disclosed aspects, or portions of these aspects, may be combined in ways not listed above. Accordingly, the invention should not be viewed as being limited to the disclosed embodiment(s). In addition, the terminology used herein is with the purpose of describing particular embodiments only, and is not intended to limit the scope of the present invention.

What is claimed is:

1. A method for performing a photometric measurement, the method comprising:
    transmitting light from a first light source to a first photodetector through a corresponding first cuvette containing a first fluid sample delivered to the first cuvette from a corresponding first inlet channel;
    transmitting light from a second light source to a second photodetector through a corresponding second cuvette containing a second fluid sample delivered to the second cuvette from a corresponding second inlet channel;

acquiring data representing said first and second fluid samples;

removing the first and second fluid samples from the corresponding first and second cuvettes through respectively corresponding first and second outlet channels to a main outlet channel; and wherein the first and second cuvettes are dimensioned to substantially prevent a formation of air-pockets therein while said first and second fluid samples flow therethrough.

2. The method according to claim 1, wherein a cuvette from the first and second cuvettes has a transition channel portion on at least one of inlet and outlet sides of said cuvette, the transition channel portion including a wall and a first bottom, said cuvette including a second bottom, the first bottom of the transition channel portion being inclined with respect to the second bottom of said cuvette at an obtuse angle between about 144 degrees and 180 degrees, wherein the wall of the transition portion is forming, with respect to a direction of fluid flow through said cuvette, at an acute angle of less than 36 degrees.

3. The method according to claim 1, wherein said removing includes:

removing a fluid from the first cuvette through the first outlet channel connected to the main outlet channel at a first point;

removing a fluid from the second cuvette through the second outlet channel connected to the main output channel at a second point; and wherein any of the first and second outlet channels is dimensioned to define a first level of resistance to a fluid flowing therethrough towards the main outlet channel, and wherein a segment of the main outlet channel defined between the first and second points is dimensioned to define a second level of resistance to the fluid flowing therethrough towards the end, a value of resistance corresponding to the first level being a multiple of a value of resistance corresponding to the second level, wherein the multiple is at least equal to the number of outlet portions in the entire fluidic network.

4. The method according to claim 3, wherein the multiple is equal to or greater than 200.

5. The method according to claim 1,
wherein the first cuvette and the second cuvette are contained in a microfluidic chip, and
wherein at least one of (i) said transmitting light from the first light source through the first cuvette, and (ii) said transmitting light from the second light source through the second cuvette includes
transmitting light through a cuvette that defines a circular projection onto said chip.

6. The method according to claim 1, further comprising preventing a flow of a fluid sample from the first and second fluid samples in a direction from the main outlet channel to a respectively-corresponding one from the first and second inlet channels.

7. The method according to claim 1, wherein said removing the first and second fluid samples includes removing the first and second fluid samples from the corresponding first and second cuvettes through respectively corresponding first and second outlet channels;
wherein the first and second cuvettes are configured to be symmetrically with respect to one another about the main outlet channel, and
wherein the first and second output channels are configured to be symmetrically with respect to one another about the main outlet channel.

8. The method according to claim 1,
wherein at least one of (i) said transmitting light from the first light source through the corresponding first cuvette containing the first fluid sample and (ii) said transmitting light from the second light source through the corresponding second cuvette containing the second fluid sample
includes transmitting light through a cuvette that is fluidly connected, to at least one of (a) a corresponding inlet channel from the first and second inlet channel and (b) a corresponding outlet channel from the first and second outlet channels, through a transition channel portion,
said transition channel portion having a cross-sectional area that is bigger than
a cross-sectional area of the corresponding inlet channel from the first and second inlet channels; and
a cross-sectional area of the corresponding outlet channel from the first and second outlet channels.

* * * * *

UNITED STATES PATENT AND TRADEMARK OFFICE
CERTIFICATE OF CORRECTION

| | |
|---|---|
| PATENT NO. | : 9,759,649 B2 |
| APPLICATION NO. | : 14/443915 |
| DATED | : September 12, 2017 |
| INVENTOR(S) | : Ramin Haghgooie et al. |

It is certified that error appears in the above-identified patent and that said Letters Patent is hereby corrected as shown below:

Column 2, Line 26, "main channel" should be --main outlet channel--.

Column 2, Line 59, "(in" should be --(ii)--.

Column 3, Line 8, "email" should be --entail--.

Column 3, Line 60, "when chamber" should be --when the chamber--.

Column 4, Line 6, "cultures multiplexed" should be --cultures in a multiplexed--.

Signed and Sealed this
Ninth Day of January, 2018

Joseph Matal
*Performing the Functions and Duties of the
Under Secretary of Commerce for Intellectual Property and
Director of the United States Patent and Trademark Office*

UNITED STATES PATENT AND TRADEMARK OFFICE
CERTIFICATE OF CORRECTION

| | |
|---|---|
| PATENT NO. | : 9,759,649 B2 |
| APPLICATION NO. | : 14/443915 |
| DATED | : September 12, 2017 |
| INVENTOR(S) | : Ramin Haghgooie et al. |

It is certified that error appears in the above-identified patent and that said Letters Patent is hereby corrected as shown below:

In the Specification

Please insert the following after the first paragraph in Column 1, Line 3:
--STATEMENT REGARDING FEDERALLY SPONSORED RESEARCH
This invention was made with government support under GM062119 awarded by the National Institutes of Health. The government has certain rights in the invention.--.

Signed and Sealed this
Ninth Day of May, 2023

Katherine Kelly Vidal
*Director of the United States Patent and Trademark Office*